United States Patent [19]

McMahan

[11] Patent Number: 5,413,555
[45] Date of Patent: May 9, 1995

[54] LASER DELIVERY SYSTEM

[76] Inventor: William H. McMahan, P.O. Box 636, 1496 State Hwy. 410, Robertson, Wyo. 82944

[21] Appl. No.: 56,209

[22] Filed: Apr. 30, 1993

[51] Int. Cl.⁶ .............................................. A61B 17/36
[52] U.S. Cl. .......................................... 606/4; 606/16; 606/19; 606/17
[58] Field of Search ........................................ 606/2–6, 606/10–13, 16–19; 607/89

[56] References Cited

U.S. PATENT DOCUMENTS

| | | | |
|---|---|---|---|
| 3,096,767 | 5/1961 | Gresser et al. | 606/17 |
| 3,315,680 | 4/1967 | Silbertrust et al. | |
| 3,528,424 | 6/1974 | Ayres | 606/19 |
| 3,982,541 | 9/1976 | L'Esperance, Jr. | |
| 4,144,888 | 3/1979 | Malyshev | 606/10 |
| 4,164,222 | 8/1979 | Prokhorov et al. | |
| 4,309,998 | 1/1982 | Aron et al. | 606/6 |
| 4,520,816 | 6/1985 | Schachar et al. | |
| 4,583,539 | 4/1986 | Karlin et al. | |
| 4,607,622 | 8/1986 | Fritch et al. | |
| 4,608,980 | 9/1986 | Aihara | 606/18 |
| 4,622,967 | 11/1986 | Schachar | |
| 4,661,958 | 4/1987 | Bowes et al. | |
| 4,865,029 | 9/1989 | Pankratov et al. | |
| 4,883,351 | 11/1989 | Weiss | 606/4 |
| 4,900,143 | 2/1990 | Bessler et al. | |
| 5,112,328 | 5/1992 | Taboada et al. | 606/5 |

FOREIGN PATENT DOCUMENTS 9217138 10/1992 WIPO ....................................... 606/4

Primary Examiner—Peter A. Aschenbrenner
Assistant Examiner—Michael Peffley
Attorney, Agent, or Firm—Thorpe, North & Western

[57] ABSTRACT

A laser delivery system which may be coupled to a stereomicroscope or camera equivalent, may be three dimensionally positioned such that a laser beam may irradiate a wide range of treatment sites from a variety of angles and distances, and where the laser beam may be positioned at an angle to the viewing axis and track along therewith. A laser delivery system including a filter/mirror system which allows only proper wavelengths to be transmitted.

29 Claims, 6 Drawing Sheets

LASER DELIVERY SYSTEM

BACKGROUND OF THE INVENTION

1. Field of the Invention

The field of the invention relates generally to the clinical use of a laser delivery device which may be coupled to a stereomicroscope or camera equivalent, or coupled to protective mirrors and/or filters.

2. Description of Related Art

Laser surgery generally requires the treating physician to illuminate and view the treatment site, and irradiate the treatment site with a laser beam. In various medical applications such as ophthalmology, neurology, dermatology or ear, nose and throat procedures, the physician typically views the treatment site through a stereomicroscope along a viewing axis within a magnified field of view. The physician may then activate the laser to irradiate the desired location.

In some existing systems, the laser delivery device is hand-held whereby the physician manually directs the laser beam to the desired location while viewing the treatment site through the stereomicroscope. This arrangement however, may not be suitable for medical applications requiring a high degree of accuracy such as procedures in the medical fields listed above.

Furthermore, a physician may desire to move the viewing axis to view different areas of the treatment site and at the same time, irradiate with the laser beam, the precise locations being viewed. Because the hand-held laser is not fixedly positioned with respect to the stereomicroscope, the laser beam cannot track along with the viewing axis as it is moved across the treatment site.

Other existing systems incorporate the laser delivery device so that it is not held by hand thereby increasing accuracy. In ophthalmic laser surgery for example, the physician typically employs a slit-lamp which includes a stereomicroscope as well as a micromanipulator which directs the laser beam to the treatment site. In this arrangement, the micromanipulator is fixedly positioned in relation to the stereomicroscope which allows the laser beam to track along with the viewing axis as it is moved.

However in systems where the laser delivery device is fixedly positioned relative to the stereomicroscope, the laser beam is typically coaxially aligned with the viewing axis, or may be moved only slightly from coaxial alignment. This limitation may prevent the treating physician from viewing the treatment site at one angle while irradiating it from another. This in turn limits flexibility in treating "hard to reach" areas such as the filtration angle of the anterior chamber of an eye. In dealing with this problem, some existing ophthalmic systems employ contact lenses which may direct the laser beam to the relatively inaccessible area. However, contact lenses generally increase the difficulty of the ophthalmic procedure being performed and may cause discomfort to the patient. While some systems may allow the laser delivery device to be positioned at an angle to the viewing axis, these systems usually provide only a limited range of angles thereby still limiting the flexibility of clinical treatment.

Where the laser delivery device is fixedly positioned in the system, limitations on flexibility in treatment also arise in connection with the characteristics of the laser beam itself. Because the laser delivery device is fixed, the focal length (working distance), cone angle, spot size and power density of the laser beam may also be limited. Thus, for example, if the physician must irradiate another treatment site located at a different distance from the system, time-consuming adjustments to vary focal length may be necessary. Furthermore, while in the ophthalmic field for example, contact lenses may be used to adjust these laser beam parameters, contact lenses generally increase the difficulty of the ophthalmic procedure.

With regard to safety, existing systems may employ fixed or movable filters, shutters, and/or dichroic mirrors to block, split or otherwise modify the laser beam which typically comprises multiple wavelengths. Dichroic mirrors may reflect the wavelength to be used for treatment onto the treatment site while absorbing other wavelengths so that the physician may view the treatment site during irradiation. Filters may also be used to protect the physician from potentially harmful wavelengths. Alternatively, a shutter may be used to completely block the physician from the laser beam.

Because filtering is not 100% efficient however, if the physician is to view the treatment site while irradiation occurs, the physician may be exposed to a fraction of undesired wavelengths. In fact, there are reports that physicians chronically exposed to slight amounts of blue wavelengths suffer from a change in color vision. Accordingly, dark filters which reduce or block different wavelengths have been used. However, dark filters greatly impair or distort the physician's field of view. Furthermore, shutters prevent the physician from viewing the treatment site during irradiation. Still further, existing systems may require an activation mechanism so that the filter or shutter blocks the viewing axis before the laser fires. Besides adding another step in the medical procedure, if this mechanism fails the physician may be exposed to harmful wavelengths.

In existing systems built for a specific laser such as an Argon blue/green laser, the mirror/filter network may have little or no effect on other wavelengths such as yellow. This is because current filters and dichroic mirrors are designed to filter or otherwise accommodate only specific wavelengths of light. Thus, if a Krypton yellow laser were mistakenly attached to a system intended for use with an Argon blue/green laser, the mirrors and filters designed to prevent transmission of the blue light would still allow yellow wavelengths to be transmitted which may result in harm to the patient or physician.

In light of the foregoing, there is a need for a laser delivery system which may be positioned at various angles and distances relative to the treatment site as well as at various angles to the viewing axis and which may track along with the viewing axis. There is also a need for a laser delivery system which includes a filter/mirror safety system to protect both the patient and treating physician.

SUMMARY OF THE INVENTION

In a first aspect of the current invention, a laser delivery system is described which may be three dimensionally positioned such that a laser beam may irradiate a wide range of treatment sites from a variety of distances and angles and where the laser beam may be positioned at an angle relative to the viewing axis of a stereomicroscope or camera equivalent and track along therewith.

In a second aspect of the current invention, a laser delivery system is described which includes a filter/mirror system to provide increased safety to both physician and patient.

DESCRIPTION OF THE PREFERRED EMBODIMENT

Though several of the figures and portions of this specification involve a slit-lamp or ophthalmology in general, the current invention is applicable to other medical applications such as neurology, dermatology or ear, nose and throat procedures. Furthermore, though much of the specification addresses the use of a laser delivery system in connection with a slit-lamp, the laser delivery system may also be used with standard stereomicroscopes or camera equivalents.

Figure 1:
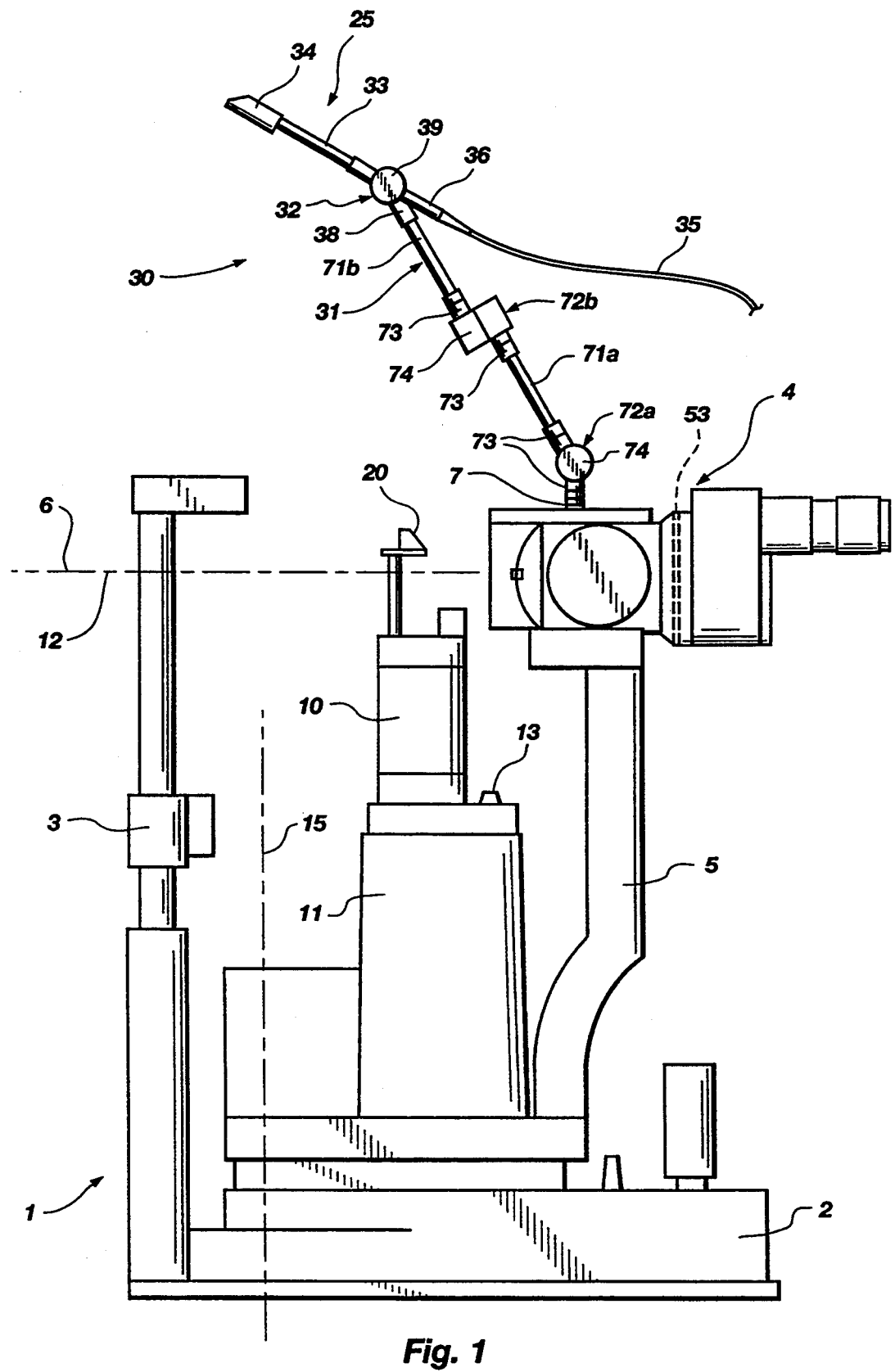
FIG. 1 is a side elevation view of a slit-lamp including an adjustable laser delivery system.

An embodiment of the present invention is illustrated in FIG. 1 in connection with a slit-lamp. As illustrated, the slit-lamp 1 includes a base 2 to which other components may be attached. A patient's chin is positioned on a chin rest 3 for steady positioning of the patient's eye during treatment.

A stereomicroscope 4 is pivotally connected to base 2 by means of support 5 so that it may rotate about axis 15. The stereomicroscope 4 allows the physician to three dimensionally view the treatment site along a viewing axis 6 within a magnified field of view. Alternatively, a camera may be incorporated into the stereomicroscope 4 so that the field of view may be photographed. An illumination system 10 is pivotally connected to base 2 by means of support 11 so that it may also rotate about axis 15 or in some applications, another axis (not shown). Illumination system 10 provides an illumination beam 12 (which in FIG. 1 is coaxial with viewing axis 6) which is directed to the desired treatment site.

Associated with stereomicroscope 4 and illumination system 10 are optics 20 and optics (not shown) within the stereomicroscope 4 which coaxially align illumination beam 12 and viewing axis 6 when neither system has been rotated as shown in FIG. 1. These optics may also provide that when one or both systems are rotated, the viewing axis 6 and illumination beam 12 are parfocal, usually at a plane at or near the treatment site.

A laser delivery system 30 which is adjustable in three dimensions, serves to deliver a laser beam to the treatment site at a variety of angles and distances. In the embodiment depicted in FIG. 1, the laser delivery system 30 is attached to the stereomicroscope 4 via flexible arm 31 which allows the laser beam to impinge on the treatment site at an angle relative to the viewing axis and to track along with the viewing axis 6 as it moves across the treatment site. Alternatively, the laser delivery system may be attached to a camera to provide the same tracking feature. As another alternative, flexible arm 31 may be attached to illumination system 10 so that the laser beam tracks along with the illumination beam 12. Stereomicroscope 4 and illumination system 10 may include port 7 or port 13 for removable attachment of the laser delivery system 30. The arm 31 may also be attached to the base 2 or other part of the slit-lamp 1 which still allows the laser beam to impinge on the treatment site from various angles and distances as well as at an angle relative to the viewing axis 6 or illumination beam 12.

Figure 1A:
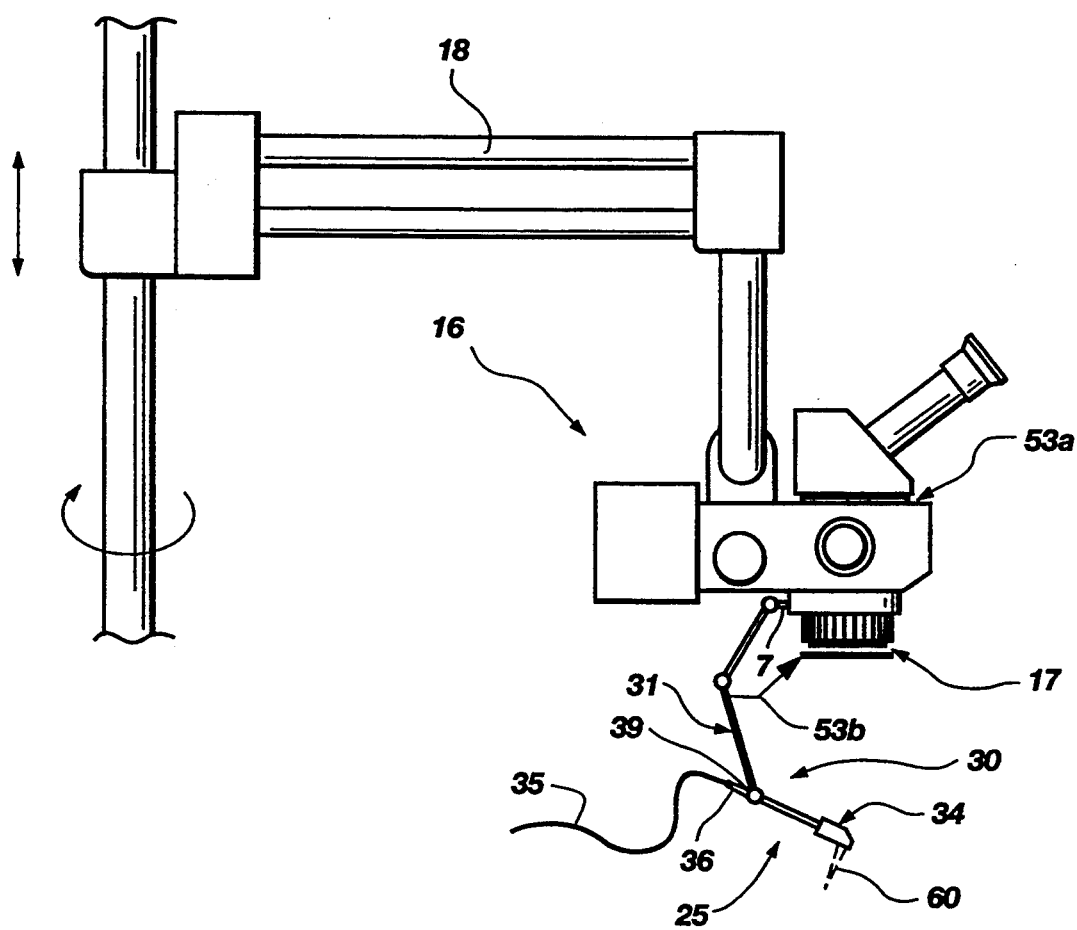
FIG. 1a is a side elevation view of a standard stereomicroscope including an adjustable laser delivery system.

As shown in figure 1a, the laser delivery system 30 may also be attached to a standard stereomicroscope 16 used in connection with various medical procedures. Stereomicroscope 16 includes objective lens 17, and is coupled to a suitable mount 18 which may provide X, Y and Z movement as shown in FIG. 1a where components similar to those of FIG. 1 are similarly numbered. Here, the laser delivery system 30 may also be removably attached via a port 7 at any location on the stereomicroscope 16 which provides the desired angular placement and tracking benefits.

Figure 2:
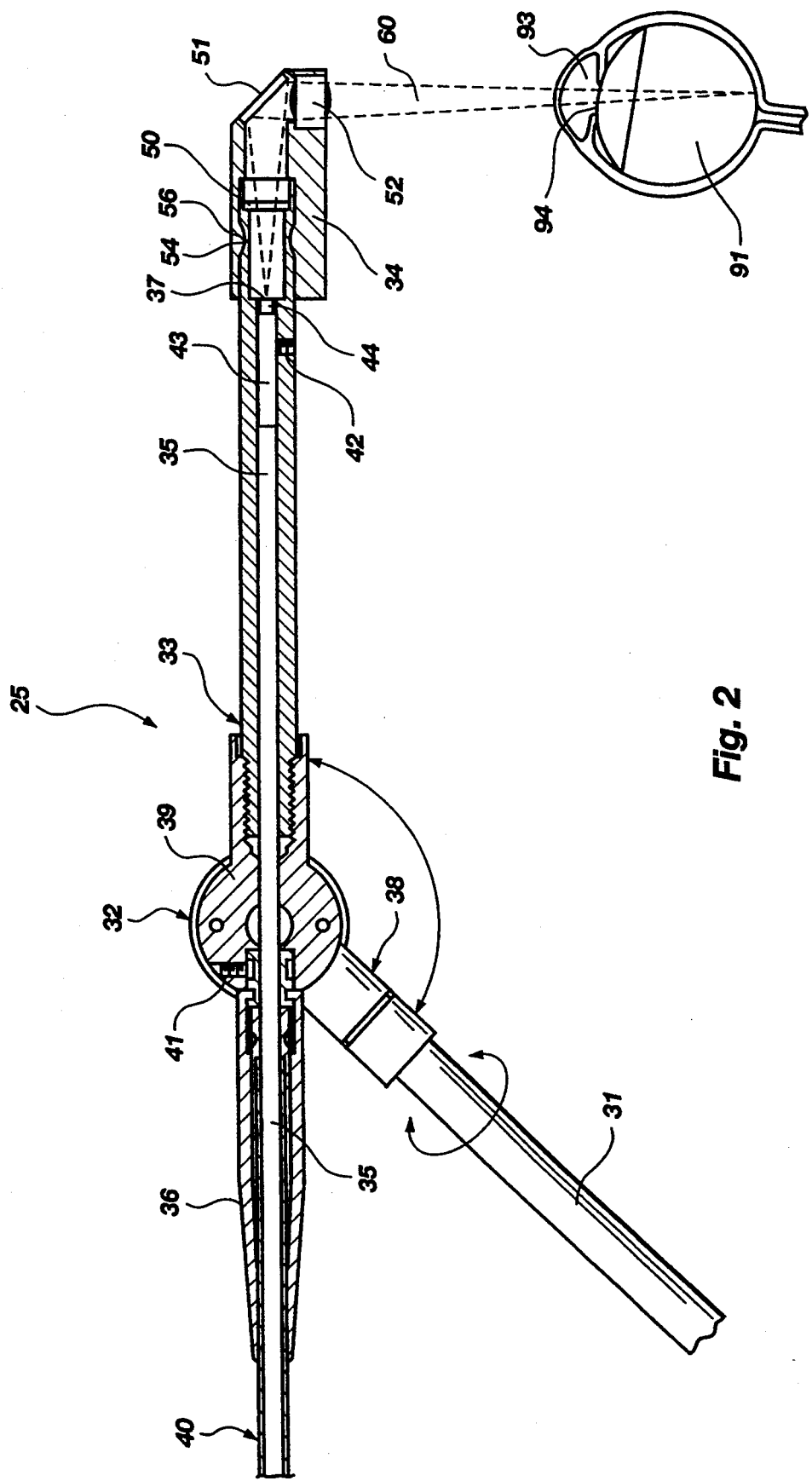
FIG. 2 is a cross-section view of several components of a laser delivery system.

As shown in FIGS. 1, 1a and 2, a laser projector 25 which directs the laser beam to the treatment site may be attached at or near the distal end of arm 31. Laser projector 25 may include pivoting member 32, stem 33 and optical head 34 whereby pivoting member 32 connects stem 33 to arm 31. Preferably, pivoting member 32 allows movement in all three dimensions. As shown by the arrows in FIG. 2, axial rotation may be provided by axial portion 38, and angular movement by pivotal portion 39. Attached to the forward end of stem 33 is optical head 34 from which the laser beam leaves the laser delivery system 30 to impinge on the treatment site.

Laser energy is provided to the laser projector 25 via a flexible optic fiber 35, the proximal end of which is attached to a laser source (not shown). As shown in FIGS. 1 and 1a, the distal end is attached to the laser projector 25. Though fiber 35 may be connected directly to pivoting member 32, preferably fiber 35 first enters receptacle 36 so that the fiber 35 does not bend too radically when pivoting member 32 is adjusted as shown by the arrows in FIG. 2. Alternatively, fiber 35 may be connected to or housed within flexible arm 31 whereby fiber 35 extends through arm 31, pivoting member 32 and into stem 33. Alternatively the laser may be housed within stem 33 or optical head 34 thus rendering optical fiber 35 unnecessary.

The laser projector 25 is now explained in more detail with reference to FIG. 2. Fiber 25 which is housed in a buffer 40 such as teflon, enters receptacle 36 which may threadably engage pivoting member 32 or be attached thereto by set screw 41. Fiber 35 extends through receptacle 36 and pivoting member 32, and enters the rear end of stem 33 which may threadably engage pivoting member 32. The distal portion of fiber 35 is housed in a ferrule 43 and set screw 42 securely positions fiber 35 in stem 33. It should be recognized that stem 33 is not necessary in that optical head 34 may be directly connected to pivoting member 32. In this alternative, pivoting member may be lengthened and may also include a set screw to securely position fiber 35. If a stem 33 is used, its length may be selected according to the physician's objectives. At its distal end 37, fiber 35 includes a quartz capillary 44.

Laser energy is transmitted through fiber 35 and diverges naturally upon exiting its distal end 37. As the laser beam diverges, it enters optical head 34 which in a preferred embodiment, rotates around the axis of stem 33 to further facilitate three-dimensional positioning capability. The laser beam passes through output filter 50, after which it is reflected by dichroic mirror 51. The laser beam then passes through focusing lens 52 which serves to produce a treatment beam 60 preferably comprising substantially only the wavelength desired to impinge on the treatment site. The output filter 50 may be removably housed by the stem 33 as shown in FIG. 2 (or by pivoting member 39 if no stem is used) or by the optical head 34.

The characteristics of the treatment beam 60 (i.e., focal length, cone angle, spot size and power density) are generally dependent on the focusing lens 52 and distance between the fiber distal end 37 and focusing lens 52. Changing either or both of these generally varies the focal length of the treatment beam as well as the other beam characteristics mentioned above. Changing one or more of the treatment beam characteristics may be desirable for irradiating different treatment sites or for performing different procedures. For example, a smaller spot size may be desired when irradiating a smaller treatment site in the eye, nose or skin, or to increase power density. Accordingly, it is preferred that the optical head 34 be removable from the laser projector 25 so that various optical heads whereby the lens 52 and distance between fiber distal end 37 and lens 52 are different to produce a treatment beam 60 having different characteristics. To facilitate easy removal, recesses 54 may be incorporated into stem 33 (or alternatively pivoting member 32 if no stem 33 is used) which accommodate corresponding knobs 56 which are incorporated into optical head 34. Alternatively, any suitable removable attachment means allowing removal of optical head 34 may be used.

As shown in FIG. 2 with respect to ophthalmology as an example, the treatment beam 60 leaves optical head 34 and enters the eye passing through anterior chamber 93 and lens 94 to irradiate a treatment site located in the posterior chamber 91. Because of the three dimensional positioning afforded by the laser delivery device 30, the treatment beam travels at the desired angle relative to the treatment site and viewing axis 6 as dictated by the position of the optical head 34. Output filter 50, dichroic mirror 51 and focusing lens 52 are discussed in more detail later in connection with the safety features of the current invention.

Figure 2A:
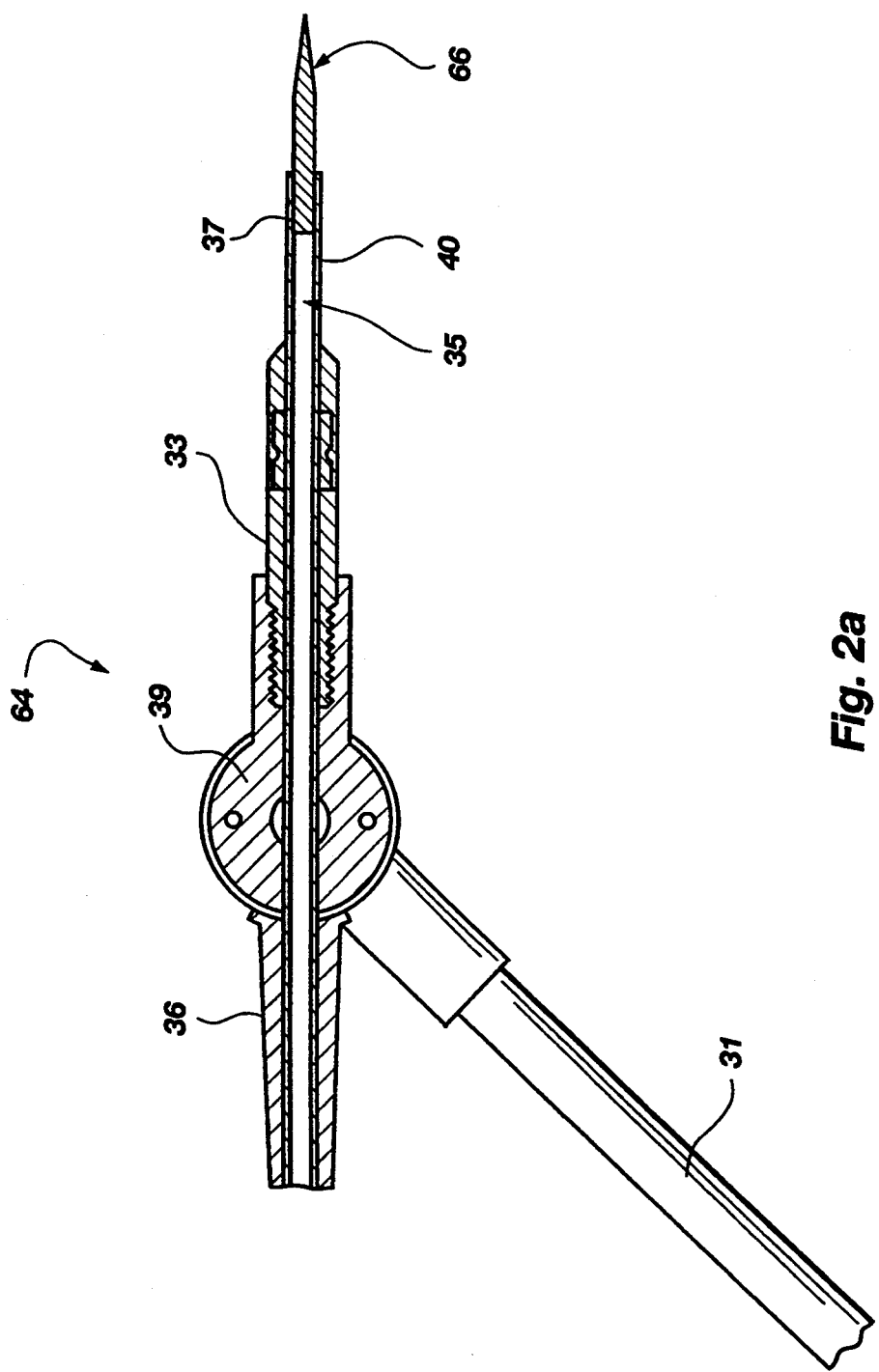
FIG. 2a is a cross-section of a laser scalpel device.

An alternative embodiment for the laser projector 25 is shown in FIG. 2a which depicts a laser scalpel device 64 which may be used in sclerostomy procedures. Components similar to those in FIGS. 1 and 1a are similarly numbered. Here the fiber 35 contained in buffer 40 may extend through pivoting member 39 and stem 33. The fiber distal end 37 interfaces with a quartz tip 66. Quartz tip 66 which is typically disposable, may be removably attached to the fiber 35 and buffer 40 as shown in FIG. 2a. Alternatively, the stem 33 may be configured so that it houses a portion of tip 66 thereby securing it to the fiber distal end 37. Preferably, interchangeable tips 66 which provide various surgical effects may be employed. The scalpel device 64 may be attached to the slit-lamp 1 of FIG. 1 or stereomicroscope 16 of figure via flexible arm 31 by means described above and thereby track along with the viewing axis as it is moved.

Figure 3A:
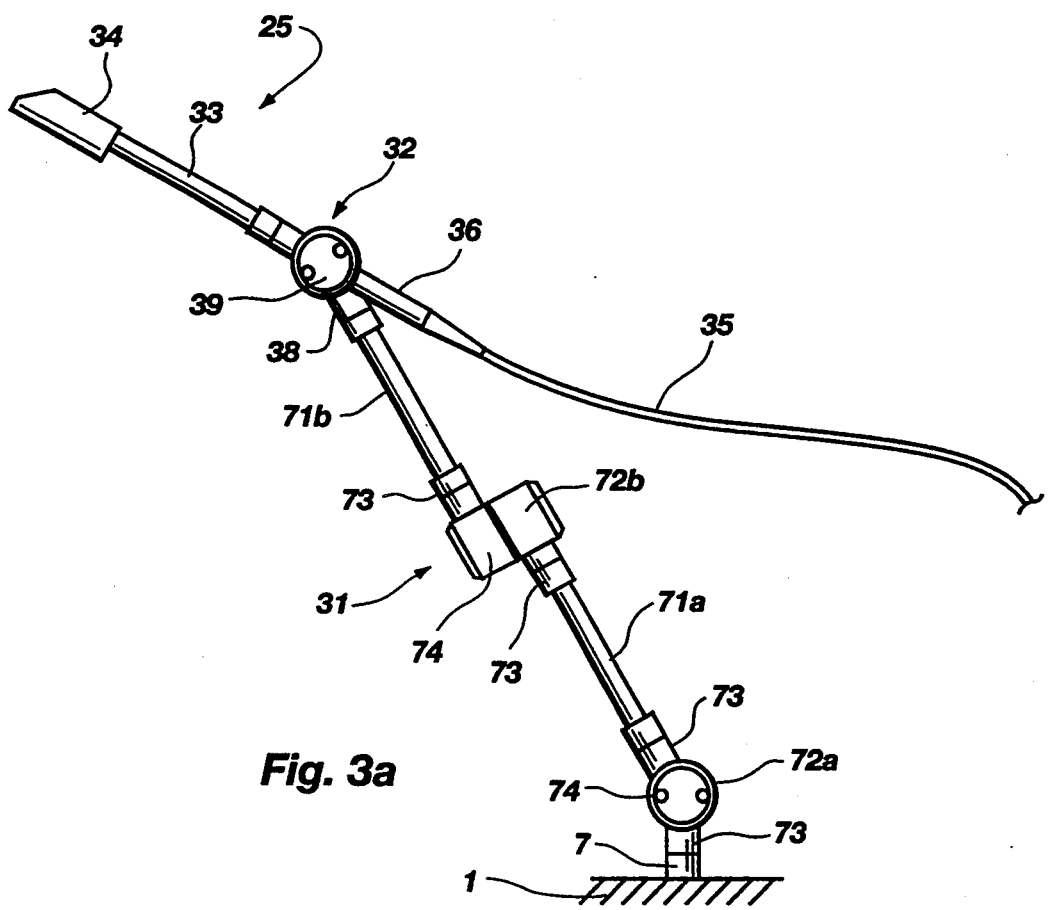
FIG. 3a is a detailed view of a flexible arm.
Figure 3B:
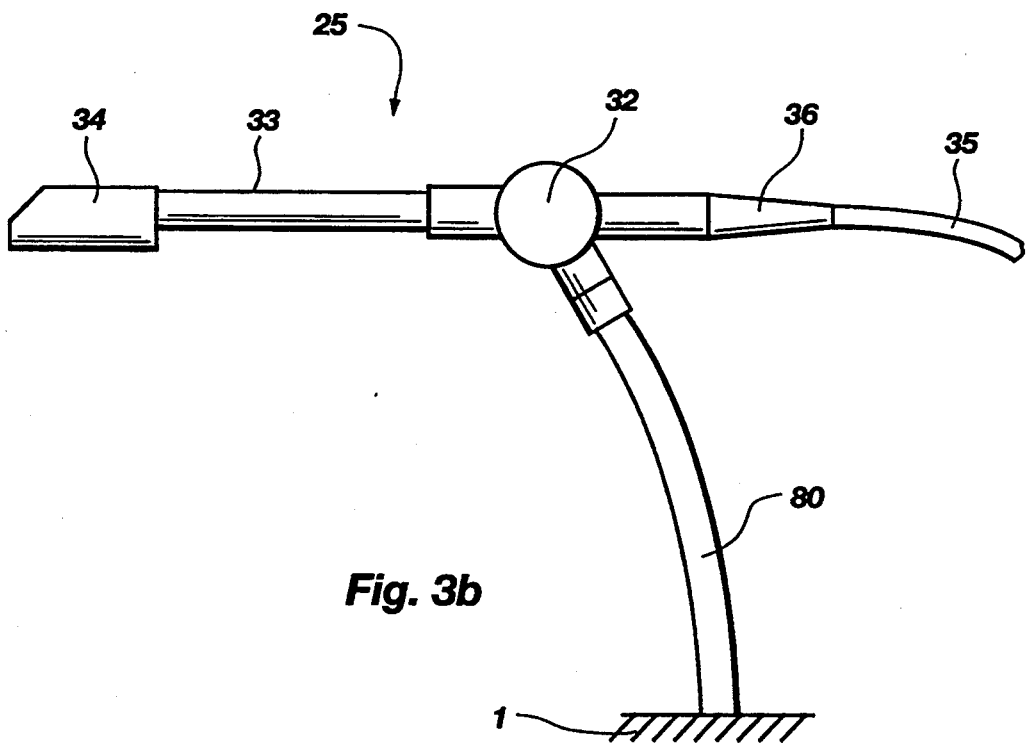
FIG. 3b is a detailed view of a flexible arm.

FIGS. 3a and 3b show alternative embodiments for flexible arm 31. Flexible arm 31 preferably allows movement in all three dimensions so that optical head 34 may be positioned to deliver treatment beam 60 to a variety of treatment sites including "hard to reach" locations within the eye, nose or other area. Three dimensional positioning also allows the treatment beam 60 to impinge on a treatment site at a variety of angles relative to the viewing axis 6.

Referring now to FIG. 3a, three-dimensional movement may be accomplished by a series of rigid or semi-rigid axial members 71a and 71b which are coupled together by connectors 72a and 72b. In the embodiment shown in FIG. 3a, connector 72a serves to attach arm 31 to the stereomicroscope 4. Alternatively however, an axial member 71 may serve to attach laser delivery system 30 to the stereomicroscope 4 or other component such as a camera. Axial member 71b attaches arm 31 to pivoting member 32. The number and size of axial members 71 and connectors 72 may vary according to the desired length of arm 31.

Though it is not necessary that each connector 72a,b exhibit three-dimensional flexibility, it is preferred that connectors 72a,b provide movement about different axes such that collectively, connectors 72 and pivoting member 32 allow optical head 34 to be positioned at any three-dimensional position. It is preferred however, that each connector 72 exhibit three-dimensional flexibility thereby enhancing the overall three-dimensional flexibility of arm 31. For example, connectors 72a,b may each comprise axial segments 73 to provide rotation about the axis of arm 31, and angular segments 74 to provide rotation in a plane substantially perpendicular thereto. Alternatively, pivoting connectors 72 may comprise ball and socket joints (not shown). Additionally, each pivoting connector 72a,b and pivoting member 32 may include a locking device (not shown) to lock each pivoting connector 72a,b and pivoting member 32 in place thereby securing the position of laser delivery system 30 after optical head 34 has been properly positioned relative to the treatment site and the viewing axis 6.

FIG. 3b shows an alternative arm 31 comprising a continuous, semi-rigid member 80. The semi-rigid member 80 may be comprised of any material which will remain in place once optical head 34 has been positioned. Here, connectors 72a,b may be unnecessary as the requisite three-dimensional movement is accomplished by the semi-rigid member 80 itself. In this embodiment, pivoting member 32 or some other type of connector may still be necessary to connect arm 31 to laser projector 25 to provide greater flexibility in three-dimensional positioning of the optical head 34. Alternatively, laser projector 25 may be adapted to engage semi-rigid member 80 without the need for pivoting member 32. It will be recognized that combinations of the embodiments of FIGS. 3a and 3b are also possible.

The alternative flexible arms 31 described above may also include servo motors to permit automated fine adjustment of the optical head's 34 position. This fine adjustment may occur after the physician has manually adjusted optical head 34 relatively close to the desired position. For example, with regard to the arm 31 of FIG. 3a, each or several of the connectors 72 and/or pivot member 32 may include servo motors which the physician may activate to fine tune the X, Y or Z coordinate position of optical head 34. One or more servo motor might be activated to move different segments of arm 31. Alternatively, the stereomicroscope 4 or 16, camera or other component to which the laser delivery system 30 is attached, may include a mechanism which provides X, Y and Z adjustment for the arm 31 and laser delivery device 30 as a whole as provided by mount 18 in FIG. 1a.

Besides providing fine adjustment for purposes of positioning the optical head 34, the use of servo motors or the like also allows the physician to move the entire arm 31 in and out of the focal plane. This in turn allows the physician to align the focal point of the laser delivery device 30 and the focal plane of the stereomicroscope 4 or 16, or camera more easily thereby saving time.

Referring again to FIG. 2, it is shown that optical fiber 35 extends through stem 33 and its distal end 37 is in proximity to optical head 34. After the laser energy leaves distal end 37 of fiber 35, it encounters in turn, output filter 50, dichroic mirror 51 and focusing lens 52.

Output filter 50 reflects the vast majority of unwanted wavelengths and transmits only the wavelength(s) desired for the medical procedure being performed. For example, many ophthalmic procedures use an Argon blue/green laser due to the ability of red tissue in the eye to absorb green wavelengths. In such ophthalmic procedures, the output filter 50 chosen would reflect substantially all wavelengths—blue and others—except green. Output filter 50 could also be configured such that an unharmful red aiming beam to aid the physician is also transmitted. A suitable lens would typically transmit green light but reflect other wavelengths including reflection of over 97% of incoming blue light. As noted earlier, the output filter 50 may be removably housed by the stem 33 (or pivoting member 39) or optical head 34.

The wavelengths which are transmitted through output filter 50 then encounter dichroic mirror 51 which further filters the laser beam. That is, any unwanted wavelengths transmitted beyond output filter 50 are absorbed by dichroic mirror 51 while desired wavelength(s) are reflected towards focusing lens 52. In the ophthalmic example employing an Argon laser, a red aiming beam could be reflected along with green wavelengths. At this point, any harmful wavelengths are reduced or substantially eliminated from the laser beam.

The laser beam then encounters focusing lens 52 which focuses the laser beam to establish treatment beam 60 for irradiation of the treatment site. Because substantially all wavelengths, except those necessary for treatment and aiming, have been reduced or substantially eliminated before the treatment beam 60 leaves optical head 34, risk to the patient is reduced or substantially eliminated.

Output filter 50 and dichroic mirror 51 also guard against transmission of laser light when optical fiber 35 has been inadvertently attached to an incorrect type of laser. In existing systems, the mirrors or filters used to eliminate harmful wavelengths are designed such that they assume the correct laser is attached. For example, existing systems intended for use with Argon blue/green lasers might reduce harmful blue wavelengths but may not reduce harmful yellow wavelengths should a yellow laser be inadvertently used.

In contrast, output filter 50 and dichroic mirror 51 would preferably operate such that the treatment beam 60 includes substantially only the green treatment beam and the red aiming beam wavelengths no matter what type of laser were attached. Thus, if a Krypton yellow laser were mistakenly attached to fiber 35, optical head 34 would produce no treatment beam 60 thus sparing the patient from potentially disastrous effects. Furthermore, the removability of the optical head 34 provides that if a different wavelength treatment beam 60 requiring use of a different laser is desired, optical head 34 and/or output filter 50 may be replaced to ensure a treatment beam of proper wavelengths. It will be recognized that the safety features of the output filter 50 and optical head 34 have medical applications other than ophthalmology such as neurosurgery, dermatology and ear, nose and throat procedures.

The laser delivery system of the current invention also addresses the harmful effects to the physician who may be exposed to laser light when viewing irradiation of the treatment site (e.g., laser light reflected back from the treatment site). As noted above, current systems may employ either a shutter which blocks the physician's field of view when the laser is fired, or a dark filter which allows the physician to view the treatment site during irradiation, but darkens the field of view drastically because the filter is necessarily designed to block a plurality of wavelengths.

The current invention overcomes these shortcomings by employing a physician's safety filter 53 which is contained in stereomicroscope 4 as shown in FIG. 1 and by location 53a in FIG. 1a. Alternatively, the physician's safety filter 53 could be housed by a camera. As another alternative, the physician's safety filter 53 could be located at location 53b and coupled to the objective lens 17 of stereomicroscope 16 as shown in FIG. 1a. Due to output filter 50 and dichroic mirror 51, substantially all wavelengths except the treatment beam 60 and the harmless red aiming beam have been eliminated by the time treatment beam 60 emerges from optical head 34. Thus the physician's safety filter need only block the wavelengths comprising the treatment beam 60. Because only one range of wavelengths need be blocked unlike current filters which necessarily block a plurality of wavelengths, the filter need not be excessively dark. The result is that the physician may safely view the treatment site as it is irradiated without the field of vision being severely darkened or distorted. The physician is thus provided with an accurate view of the laser's effects on the treatment site as they occur.

Figure 4A:
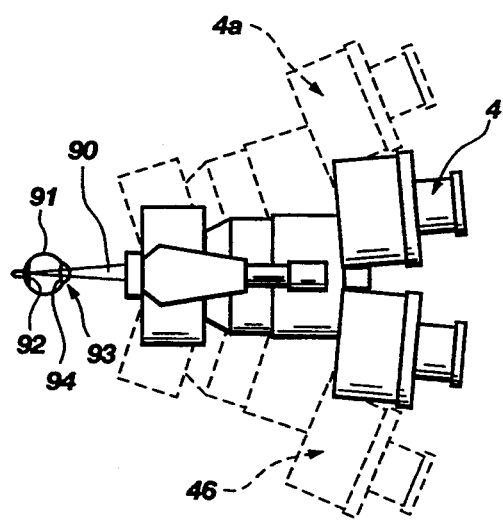
FIGS. 4a through 4d depict the greater range of access to peripheral locations in the eye afforded by an adjustable laser delivery device.
Figure 4B:
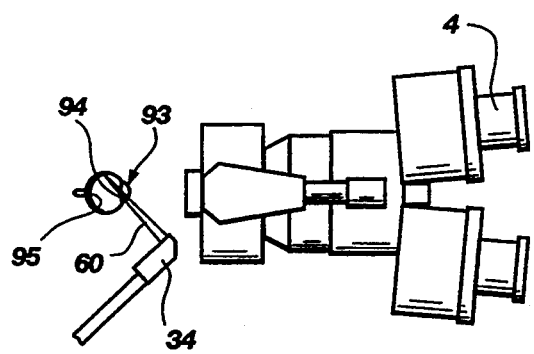

Several of the advantages that the laser delivery system 30 provides over existing laser delivery systems and clinical techniques are now described. One advantage is that "hard to reach" treatments sites such as those contained in the peripheral portions of the eye or nose are accessed more easily. This advantage with respect to an eye is shown in FIGS. 4a–4d. The solid lines in FIG. 4a depicts a top view of stereomicroscope 4 with a laser micromanipulator (not separately shown) incorporated therein as embodied by the majority of existing slit-lamps. The dashed lines indicate the two ends 4a and 4b of the range of motion of the stereomicroscope 4 where the physician may view the posterior chamber 91 as dictated by the width of the lens 94. FIG. 4b shows a top view of a comparable stereomicroscope 4 without a micromanipulator, but with the optical head 34 of the current invention. Though the optical head 34 is not shown as connected to stereomicroscope 4 in FIG. 4b, in practice, arm 31 may attach optical head 34 to the stereomicroscope 4 via port 7 as described above.

As can be seen in FIG. 4a, the laser beam 90 may impinge on only a limited horizontal range in the posterior chamber 91 as indicated by the thick line 92. Furthermore, impingement in many areas of the anterior chamber 93 cannot be achieved. The range of locations which may be impinged is essentially limited by the pivotal capability of the stereomicroscope 4 and the width of the eye's lens 94. That the micromanipulator may adjust the laser beam's direction a small amount away from coaxial alignment with viewing axis 6 does not overcome this limitation. Furthermore, though a contact lens may be used to increase the number of accessible treatment sites, its used generally increases the difficulty of the procedure and may cause discomfort to the patient.

On the other hand, the optical head 34 as shown in FIG. 4b provides that the treatment beam 60 has access to a far greater range 95 of treatment sites in the posterior and anterior chambers without the use of a contact lens. First, direction of treatment beam 60 is not dependent on the pivotal range of movement of the stereomicroscope 4. Second, the optical head 34 may be easily positioned closer to the eye so that the width of the lens 94 does not restrict access within the eye. While a contact lens may still be necessary to view the treatment site whereby the treatment beam 60 still passes therethrough, the ability to adjust the treatment beam angle still provides an extra degree of freedom currently unavailable with existing systems. Furthermore a contact lens may be unnecessary for viewing or irradiating in certain other procedures which may include treatment of peripheral vitreous hemorrhaging, peripheral iridoplasty or iridotomy.

Figure 4C:
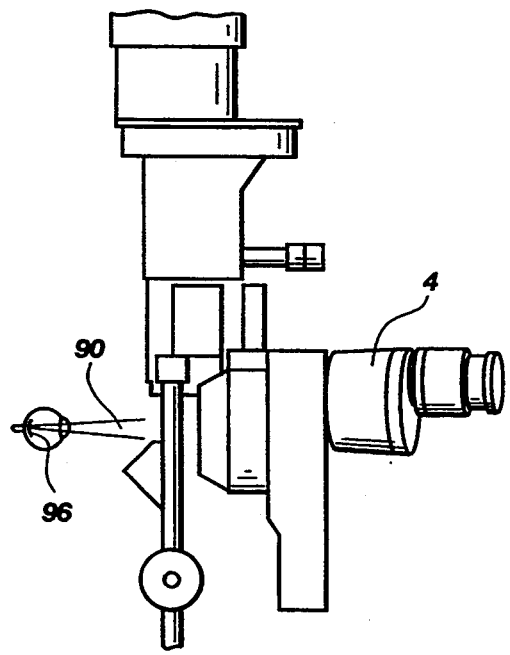
Figure 4D:
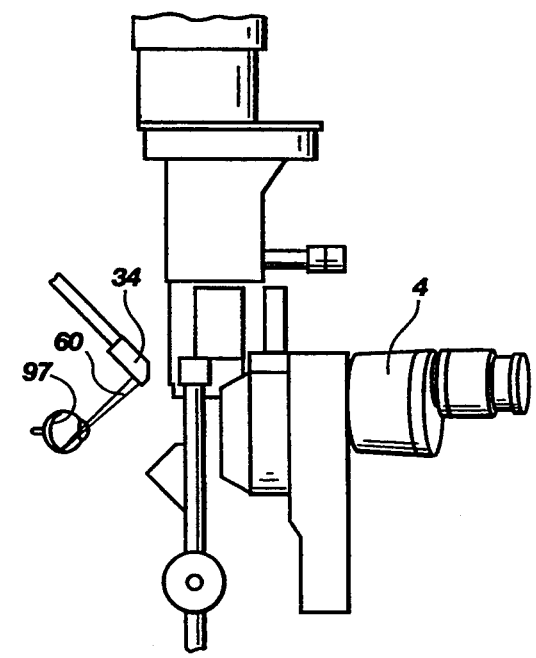

FIGS. 4c and 4d show respective side elevation views of the two slit-lamps described in FIGS. 4a and 4b. As can be seen from FIG. 4c, the vertical range 96 of treatment sites accessible by laser beam 90 is even further limited because the stereomicroscopes of existing slit-lamps do not typically pivot in a vertical plane. However, in FIG. 4d, which includes the optical head 34 of the preferred embodiment as in FIGS. 1 and 4b, a far greater range 97 of treatment sites is accessible by treatment beam 60.

Another advantage is that because the flexible arm 31 may be adjusted in all three dimensions, the physician may position the optical head 34 at a random point in space and at an adjustable angle relative to the treatment site and viewing axis 6. Optical head 34 may also be positioned coaxially with the viewing axis 6 with the use of mirrors (not shown) to guide the treatment beam 60 in similar fashion as in existing micromanipulators.

Another advantage is that the characteristics of the treatment beam 60 (i.e., focal length, cone angle, spot size and power density) may be routinely varied by changing optical heads 34. As an example in the ophthalmic field, an optical head 34 may be easily attached which produces a treatment beam with a short focal length and large cone angle for procedures where the waist of the treatment beam 60 should be sufficiently large as it passes through the cornea to avoid burning thereof, while the spot size and concomitant power density be sufficient upon arriving at the treatment site to achieve the desired tissue effects. The interchangeability of optical heads eliminates time-consuming extra procedural steps and adjustments which occur with existing systems when different treatment sites are to be irradiated or different procedures are to be performed. Easy removal of optical head 34 also allows output filter 50 to be replaced in preparation of using another color laser. If the output filter 50 is contained in the optical head 34, another optical head 34 might contain another output filter 50. Alternatively, if the output filter 50 is housed in the stem 33 (or pivoting member 39) removal of the optical head 34 provides access to the output filter 50 for its replacement.

Another advantage is that because optical head 34 may be fixedly positioned relative to the viewing axis 6, the treatment beam 60 may track along with viewing axis 6 as different areas of the treatment site are viewed. This allows the physician to irradiate, at various angles, the precise locations which are being viewed even as the viewing axis 6 is moved.

Another advantage is that three-dimensional positioning of the optical head 34 relative to the stereomicroscope 4 generally permits greater flexibility for clinical applications. For example, different treatment beam angles are routinely available and a contact lens may be rendered unnecessary in certain ophthalmic procedures. Furthermore, laser projector 25 may be positioned out of the physician's way so that it does not block the field of view or otherwise constrict the physician.

Other advantages regarding safety are that both the patient is protected from potentially harmful wavelengths as is the physician who may view irradiation as it occurs without the distortion of existing dark filters. Furthermore, if an incorrect laser is attached to the laser delivery system 30, no light will emanate from the optical head.

Thus, a laser delivery system has been shown and described. Though certain examples and advantages have been disclosed, further advantages and modifications may become obvious to those skilled in the art from the disclosures herein. The current invention therefore is not to be limited except in the spirit of the claims that follow.

What is claimed is:

1. A laser delivery system for use by a user and in connection with a stereomicroscope having a viewing axis, said stereomicroscope having a first side, a second side, a front side, and a back side, the laser delivery system also including a laser generating device producing an output conveyed to the laser delivery system comprising:

a laser projector which generates a treatment beam to impinge on a treatment site, the output of the laser generating device being connected to the laser projector the laser projector comprising:

an arm selectively attachable at a first end to the stereomicroscope, and selectively attachable at a second end to support the laser projector, the arm being flexible such that the laser projector may be moved in three dimensions and oriented in any desired orientation relative to the treatment site and such that the laser projector can be selectively moved to any one of at least the first side, second side and front side of the stereomicroscope by an action of the user; and a pivoting member, the pivoting member being attached to the second end of the art, the pivoting member having an interior channel therethrough;

an optical head having an entrance end to receive incoming laser light, and an exit end to direct the treatment beam to the treatment site, the entrance and being coupled to the pivoting member; and an optical fiber for transmitting laser light and having a proximal end and distal end, the proximal end being adapted to attach to a laser source the fiber extending through the pivoting member such that the distal end is in proximity to the entrance end of the optical head.

2. The laser delivery system of claim 1, further comprising:

an optical fiber having a distal end coupled to the laser projector, the optical fiber being capable of transmitting laser light and having a proximal end adapted to connect to a laser source.

3. The laser delivery system of claim 1 wherein the arm allows the treatment beam to impinge the treatment site at a selected angle relative to the viewing axis.

4. The laser delivery system of claim 1 wherein the arm comprises means for tracking the treatment beam along with the viewing axis as the viewing axis is moved.

5. The laser delivery system of claim 1, the laser projector further comprising:
a laser scalpel device.

6. The laser delivery system of claim 1 wherein the pivoting member:
rotates about an axis of the arm; and
pivots in a plane substantially perpendicular to the axis of the arm.

7. The laser delivery system of claim 1, further comprising:
a stem which couples the optical head to the pivoting member, the stem including a forward end near the optical head and a rearward end near the pivoting member.

8. The laser delivery system of claim 7 wherein the optical head is rotatably mounted to the forward end of the stem.

9. The laser delivery system of claim 7 wherein the optical head is removably attached to the forward end of the stem.

10. The laser delivery system of claim 7, further comprising:
an output filter mounted near the forward end of the stem;
a dichroic mirror mounted in the optical head between the entrance end and exit end; and
a focusing lens mounted in the optical head near the exit end.

11. The laser delivery system of claim 10, wherein:
the output filter transmits desired wavelengths and substantially reflects all other wavelengths; and
the dichroic mirror reflects desired wavelengths and substantially absorbs all other wavelengths.

12. The laser delivery system of claim 11 wherein the laser delivery system further generates an aiming beam, the aiming beam passing through the output filter and reflected by the dichroic mirror.

13. The laser delivery system of claim 1 wherein the arm comprises:
at least one rigid axial member; and
at least one connector coupled to the at least one axial member, the at least one connector allowing the orientation of the axial member to be altered.

14. The laser delivery system of claim 13 wherein:
the at least one axial member and connector are coupled together by a ball and socket arrangement.

15. The laser delivery system of claim 13 wherein at least one of the connectors further comprises a lock.

16. The laser delivery system of claim 1 further comprising:
an automated adjustment means coupled to the arm, the automated adjustment means adjusting the orientation of the arm and cooperating to position the laser projector in the desired location.

17. The laser delivery system of claim 1 wherein the arm further comprises a continuous semi-rigid axial member.

18. A slit-lamp for observing and providing treatment to an eye carried out by a user, comprising:

a stereomicroscope providing a magnified image of the eye along a viewing axis, said stereomicroscope having a first side, a second side, a front side, and a back side;

a laser delivery system mounted to the slit-lamp for generating a treatment beam, the laser delivery system including means for receiving light produced by a laser generating device, the treatment beam being configured to impinge on a treatment site in the eye, the laser delivery system including a support structure and further comprising:

an optical head having an entrance end to receive incoming laser light, and an exit end to direct the treatment beam to the treatment site, the entrance end being coupled to the pivoting member; and an optical fiber for transmitting laser light and having a proximal end an distal end, the fiber being adapted to attach to a laser source at its proximal end, and extending through the pivoting member such that the distal end is in proximity to the entrance end of the optical head; and means, included in the support structure, for allowing the laser delivery system to be moved in three dimensions and positioned in any orientation relative to the treatment site and such that a laser projector can be selectively positioned on any one of at least the first side, second side and front side of the stereomicroscope by an action of the user, wherein the support structure includes an arm having a first end and second end, the arm being flexible to provide movement in three dimensions, the arm being attached to the first end to the slit-lamp, and attached at the second end to a pivoting member, the pivoting member having an interior channel therethrough.

19. The slit-lamp of claim 18 wherein the support structure comprises means for allowing the treatment beam to impinge the treatment site at a selected angle relative to the viewing axis.

20. The slit-lamp of claim 18 wherein the laser delivery system is mounted to the stereomicroscope and comprises means for tracking the treatment beam along with the viewing axis as the viewing axis is moved.

21. The clip-lamp of claim 18 wherein the pivoting member:
rotates about an axis of the arm; and
pivots about an axis substantially perpendicular to the axis of the arm.

22. The slit-lamp of claim 18, further comprising:
a stem which couples the optical head to the pivoting member, the stem including a forward end near the optical head, a read end near the pivoting member, and an axial channel extending therebetween.

23. The slit-lamp of claim 22 wherein the optical head is rotatable mounted to the forward end of the stem.

24. The slit-lamp of claim 22 wherein the optical head is removably attached to the forward end of the stem.

25. The slit-lamp of claim 24 wherein the optical head further comprises:
an output filter mounted in proximity to the entrance end, the output filter transmitting desired wavelengths of laser light and substantially reflecting all other wavelengths of laser light;
a dichroic mirror mounted between the output filter and exit end, the dichroic mirror reflecting desired wavelengths of laser light and substantially absorbing all other wavelengths of laser light; and a focusing lens mounted in proximity to the exit end.

26. The slit-lamp of claim 18 further comprising:
a physician's safety filter mounted within the stereomicroscope along the viewing axis whereby the physician's safety filter blocks wavelengths of light comprising the treatment beam.

27. The slit-lamp of claim 26 wherein the laser delivery system further comprises means for generating an aiming beam coaxially with the treatment beam, wherein the aiming beam passes through the output filter, dichroic mirror and the physician's safety filter.

28. A laser delivery system for use in connection with a stereomicroscope having a viewing axis and a laser generating device producing an output, comprising;
a laser projector which generates a treatment beam to impinge on a treatment site, the output of the laser generating device being connected to the laser projector;
an arm selectively attached a first end to the stereomicroscope, and selectively attached a second end to support the laser projector, the arm being flexible such that the laser projector may be moved in three dimensions and oriented in any desired orientation relative to the treatment site;
a pivoting member, the pivoting member being attached to the second end of the arm, the pivoting member having an interior channel therethrough;
an optical head having an entrance end to receive incoming laser light, and an exit end to direct the treatment beam to the treatment site, the entrance end being coupled to the pivoting member; and
an optical fiber for transmitting laser light and having a proximal end and a distal end, the proximal end being adapted to attach to a laser source, the fiber extending through the pivoting member such that the distal end is in proximity to the entrance end of the optical head.

29. A slit-lamp for observing and providing treatment to an eye carried out by a user, comprising:
a stereomicroscope providing a magnified image of the eye along a viewing axis, said stereomicroscope having a first side, a second side, a front side, and a back side;
a laser delivery system mounted to the slit-lamp for generating a treatment beam, the laser delivery system including means for receiving light produced by a laser generating device, the treatment beam being configured to impinge on a treatment site in the eye, the laser delivery system including a support structure, the support structure including an arm having a first end and second end, the arm being flexible to provide movement in three dimensions, the arm being attached at the first end to the slit-lamp and attached to the second end to a pivoting member, the pivoting member having an interior channel therethrough;
means, included in the support structure, for allowing the laser delivery system to be moved in three dimensions and positioned in any orientation relative to the treatment site by an action of the user;
an optical head having an entrance end to receive incoming laser light, and an exit end to direct the treatment beam to the treatment site, the entrance end being coupled to the pivoting member; and
an optical fiber for transmitting laser light and having a proximal end and distal end, the fiber being adapted to attach to the laser generating device at its proximal end, and extending through the pivoting member such that the distal end is in proximity to the entrance end of the optical head.

* * * * *